US008586795B2

(12) United States Patent
Hugo et al.

(10) Patent No.: US 8,586,795 B2
(45) Date of Patent: Nov. 19, 2013

(54) METHYL-SUBSTITUTED TETA COMPOUNDS

(75) Inventors: Randolf Hugo, Dirmstein (DE); Johann-Peter Melder, Böhl-Iggelheim (DE); Robert Baumann, Mannheim (DE); Alfred Oftring, Bad Dürkheim (DE); Boris Buschhaus, Mannheim (DE); Gordon Brasche, Frankfurt (DE); Sebastian Ahrens, Wiesloch (DE); Peter Pfab, Neustadt (DE)

(73) Assignee: BASF SE (DE)

( * ) Notice: Subject to any disclaimer, the term of this patent is extended or adjusted under 35 U.S.C. 154(b) by 50 days.

(21) Appl. No.: 13/378,091

(22) PCT Filed: Jun. 14, 2010

(86) PCT No.: PCT/EP2010/058287
§ 371 (c)(1),
(2), (4) Date: Dec. 14, 2011

(87) PCT Pub. No.: WO2010/146009
PCT Pub. Date: Dec. 23, 2010

(65) Prior Publication Data
US 2012/0101303 A1   Apr. 26, 2012

(30) Foreign Application Priority Data

Jun. 18, 2009  (EP) .................................. 09163055

(51) Int. Cl.
*C07C 209/46* (2006.01)
*C07C 209/62* (2006.01)

(52) U.S. Cl.
USPC ........................................................ 564/487

(58) Field of Classification Search
USPC ........................................................ 564/487
See application file for complete search history.

(56) References Cited

U.S. PATENT DOCUMENTS

| | | |
|---|---|---|
| 2,743,243 A | 4/1956 | DeGroote et al. |
| 2,828,276 A | 3/1958 | DeGroote et al. |
| 2,839,480 A | 6/1958 | Ott et al. |
| 3,026,203 A | 3/1962 | Chambers et al. |
| 3,240,664 A | 3/1966 | Earle et al. |
| 3,825,521 A | 7/1974 | Izawa et al. |
| 4,044,053 A | 8/1977 | Brennan et al. |
| 5,530,127 A | 6/1996 | Reif et al. |
| 5,696,048 A | 12/1997 | Breitscheidel et al. |
| 6,297,394 B1 | 10/2001 | Voit et al. |
| 6,518,449 B1 | 2/2003 | Boschat et al. |
| 2002/0058842 A1 | 5/2002 | Ansmann et al. |
| 2006/0041170 A1 | 2/2006 | Jonas et al. |
| 2010/0121064 A1 | 5/2010 | Dahmen et al. |

FOREIGN PATENT DOCUMENTS

| | | |
|---|---|---|
| DE | 1148866 B | 5/1963 |
| EP | 0222934 A1 | 5/1987 |
| EP | 696572 A1 | 2/1996 |
| EP | 742045 | 11/1996 |
| EP | 963975 A1 | 12/1999 |
| EP | 1 209 146 A1 | 5/2002 |
| JP | 2008056849 | 3/2008 |
| WO | WO-99/33561 A1 | 7/1999 |
| WO | WO-99/44984 A1 | 9/1999 |
| WO | WO-2008/104582 A2 | 9/2008 |

OTHER PUBLICATIONS

International Search Report for PCT/EP2010/058287 mailed Sep. 17, 2010.
Database Beilstein (Online) Beilstein Institute for Organic Chemistry, Frankfurtmain, DE, 1966, XP002598989 Database accession No. RID:4054501.
Database Registry (Online) Chemical Abstracts Service, Columbus, Ohio, Nov. 16, 1984, XP002598988 Database accession No. RN:65379-59-1.
Database Registry (Online) Chemical Abstracts Service, Columbus, Ohio, Oct. 1, 2004, Database accession No. RN:755713-79-2.
Database WPI Week 200827 Thomson Scientific, London, GB; AN 2008-D75610 & JP2008056849 (Tosoh Corp) Mar. 13, 2008.
Translation of International Preliminary Report on Patentability of PCT/EP2010/058287 mailed Dec. 20, 2011.

*Primary Examiner* — Brian J Davis
(74) *Attorney, Agent, or Firm* — Novak Druce Connolly Bove + Quigg LLP

(57) ABSTRACT

The invention relates to a process for preparing triethylenetetramine substituted by at least one methyl group (Me-TETA or methyl-substituted TETA compounds). Me-TETA is prepared by hydrogenating biscyanomethylimidazolidine (BCMI) in the presence of a catalyst. The present invention further relates to methyl-substituted TETA compounds as such. The present invention further relates to the use of methyl-substituted TETA compounds as a reactant or intermediate in the production of, for example, coatings or adhesives.

18 Claims, No Drawings

METHYL-SUBSTITUTED TETA COMPOUNDS

CROSS-REFERENCE TO RELATED APPLICATIONS

This application is a national stage application (under 35 U.S.C. § 371) of PCT/EP2010/058287, filed Jun. 14, 2010, which claims benefit of European application 09163055.8, filed June 18, 2009.

BACKGROUND OF THE INVENTION

The invention relates to a process for preparing triethylenetetramine substituted by at least one methyl group (Me-TETA or methyl-substituted TETA compounds). Me-TETA is prepared by hydrogenating biscyanomethylimidazolidine (BCMI) in the presence of a catalyst. The present invention further relates to methyl-substituted TETA compounds as such. The present invention further relates to the use of methyl-substituted TETA compounds as a reactant or intermediate in the production of, for example, coatings or adhesives.

The preparation of (unsubstituted) triethylenetetramine (TETA) is general knowledge. TETA belongs to the group of the ethyleneamines, the best known representatives of which are the short-chain ethylenediamine (EDA) and diethylenetriamine (DETA). Ethyleneamines are suitable as starting materials for the production of numerous end products in different branches of industry, for example in the epoxy sector. For instance, ethyleneamines are suitable for producing coatings, adhesives, adhesion promoters, plastic or polymers. The chemical composition and the properties of the end products thus produced are influenced greatly by the selection of the ethyleneamine as the reactant or intermediate for the production of such end products.

TETA is obtained, among other ways, as a by-product in the preparation of short-chain ethyleneamines such as EDA and DETA. For instance, EP-A 222 934 relates to a process for preparing higher alkylenepolyamines by reacting a vicinal dihaloalkane with an excess of ammonia in the aqueous phase with addition of a strong base to form an imine intermediate, which is then reacted with an alkylenepolyamine to form the higher alkylenepolyamine. A suitable vicinal dihaloalkane is especially ethylenedichloride (EDC or 1,2-dichloroethane). The alkylenepolyamines used are especially ethylenediamine or higher ethyleneamines such as DETA, but also TETA and tetraethylenepentamine (TEPA). These processes (EDC processes) give a mixture of different ethyleneamines (linear ethyleneamines such as EDA, DETA, TETA, TEPA or higher ethyleneamines, and cyclic derivatives such as piperazine (Pip) or aminoethylpiperazine (AEPip)). According to which ethyleneamine is added to the EDC and NH$_3$ reactants, the reaction mixture comprises a corresponding proportion of higher ethyleneamines.

In addition, there are also selective processes for preparing TETA. Such a process is described in WO 2008/104582, according to which TETA is prepared by hydrogenating ethylenediaminediacetonitrile (EDDN) over a catalyst. EDDN in turn is obtainable by reacting EDA with formaldehyde and hydrogen cyanide (HCN). The reaction of EDA with formaldehyde and hydrogen cyanide can be performed in different variants, for example to form the formaldehyde cyanohydrin (FACH) intermediate, by first reacting formaldehyde and hydrogen cyanide in the absence of EDA. According to the selection of the reactant concentrations, as well as EDDN, the corresponding mononitrile compound ethylenediaminemonoacetonitrile (EDMN) can be formed additionally. The preparation of TETA by direct hydrogenation of EDDN is shown in scheme 1 below:

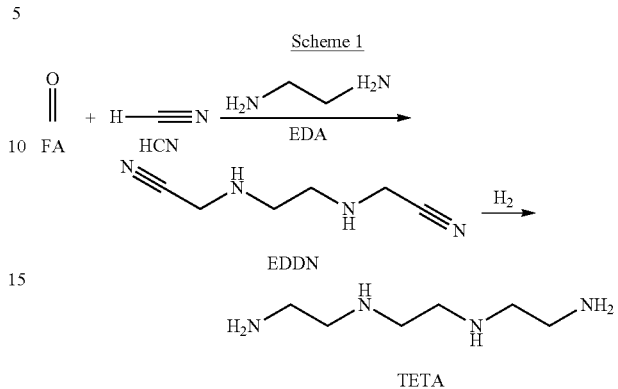

An alternative process for direct hydrogenation of EDDN is described in US-A 2006/0041170, according to which, before the hydrogenation, different protecting groups are attached to the two amino functions of EDDN. After the hydrogenation, the protecting groups are removed again to form (unsubstituted) TETA salts. For instance, two different protecting group methods using benzaldehyde are disclosed, in which no hydrogen but lithium aluminum hydride is used. In a third method, the hydrogenation is performed with hydrogen in the presence of a Boc protecting group. A disadvantage of the process described in US-A 2006/0041170 is especially that it is a multistage hydrogenation process, in which the EDDN reactant used first has to be chemically derivatized (protecting groups) in order to perform the hydrogenation. After the hydrogenation, the protecting groups have to be eliminated again in several reaction steps, which initially give (unsubstituted) TETA as the salt and not in the free base form.

BRIEF SUMMARY OF THE INVENTION

It is an object of the present invention to provide novel TETA derivatives which possess at least one methyl substituent, and a process for preparing these novel TETA derivatives. Using these novel methyl-substituted TETA compounds, it is thus also possible to prepare novel conversion products which possess modified performance properties.

The object is achieved by a process for preparing triethylenetetramine substituted by at least one methyl group (Me-TETA), comprising the hydrogenation of biscyanomethylimidazolidine (BCMI) in the presence of a catalyst.

A DETAILED DESCRIPTION OF THE INVENTION

The process according to the invention has the advantage that it is thus possible in a selective manner to produce another substance class of TETA derivatives (i.e. methyl-substituted TETA compounds/Me-TETA). Me-TETA is obtained with high conversion and/or high selectivity. With the inventive methyl-substituted TETA compounds, it is in turn possible to selectively prepare conversion products with a new chemical composition and hence also modified properties.

In the context of the present invention, a triethylenetetramine substituted by at least one methyl group (Me-TETA) is understood to mean any triethylenetetramine (TETA) derivative in which one, two or more of the hydrogen atoms bonded to the four amino functions of the unsubstituted TETA are substituted by the corresponding number of methyl groups ($CH_3$—).

Me-TETAs according to the present invention are shown by way of example in scheme 2 below as compounds (2) to (13).

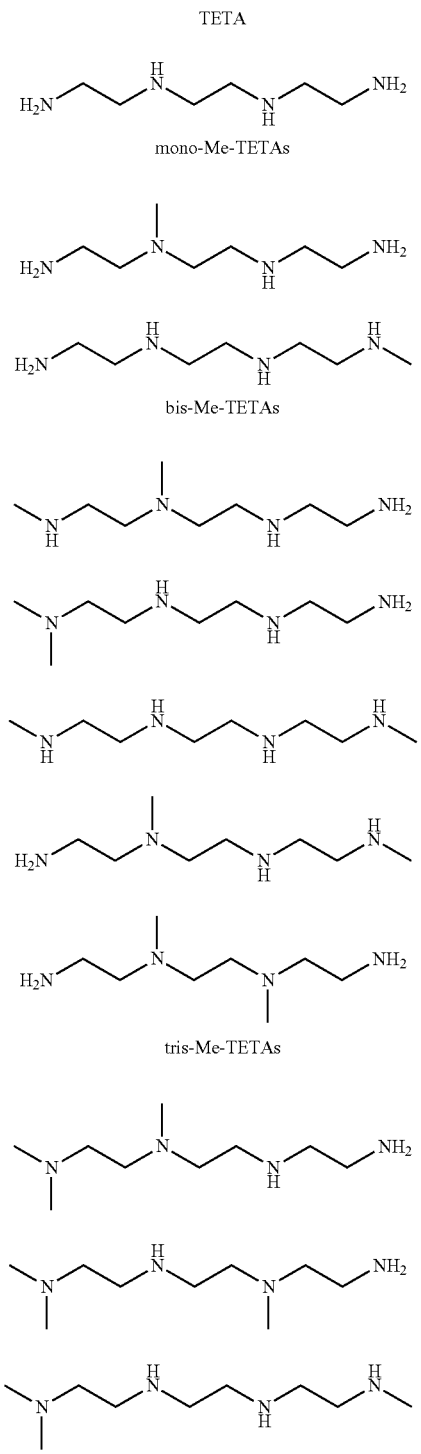

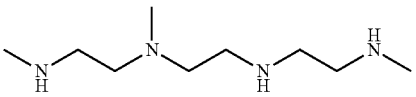

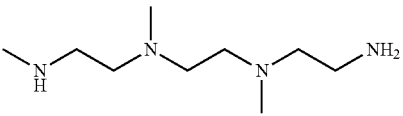

Depending on the hydrogenation conditions selected, such as pressure, temperature or catalyst, it is possible in the process according to the invention for the hydrogenation of BCMI to form Me-TETAs with a different number of methyl groups. Additionally also obtained as a by-product is unsubstituted TETA (scheme 2: compound 1). As can be inferred from scheme 2, it is possible in the process according to the invention to form Me-TETAs with one (mono-Me-TETA; compounds 2 and 3), two (bis-Me-TETA; compounds 4 to 8) and three methyl substituents (tris-Me-TETA; compounds 9 to 13). In addition, it is also possible to form Me-TETAs in which four, five or all six hydrogen atoms of the unsubstituted TETA are substituted by methyl groups as by-products.

The hydrogenation of BCMI in the process according to the invention generally gives a mixture of at least two Me-TETAs according to the above scheme 2. The ratio of the individual Me-TETA compounds is variable, since it is influenced greatly by the other hydrogenation parameters such as pressure, temperature or catalyst. The hydrogenation parameters can be selected such that one or more of the Me-TETAs shown in scheme 2 are prepared selectively. This means in turn that, according to the selection of the hydrogenation parameters, some of the Me-TETAs shown in scheme 2 are not formed at all, provided that one or more of the remaining Me-TETAs is prepared selectively. When, in the process according to the invention, the hydrogenation of BCMI gives a mixture comprising at least 2 Me-TETAs, the individual Me-TETAs can be separated from one another or isolated from the Me-TETA mixture by methods known to those skilled in the art.

The present invention thus provides both the process described in detail hereinafter for preparing triethylenetetramine substituted by at least one methyl group (Me-TETA), and the corresponding Me-TETA as such. The Me-TETA is preferably selected from triethylenetetramine substituted by one methyl group (mono-Me-TETA), triethylenetetramine substituted by two methyl groups (bis-Me-TETA), or triethylenetetramine substituted by three methyl groups (tris-Me-TETA).

The inventive Me-TETA is more preferably a mono-Me-TETA. More particularly, the Me-TETA is selected from N-2-aminoethyl-N'-(2-N'''-methylaminoethyl)-1,2-ethanediamine (sec-Me-TETA) and N-2-aminoethyl-N-methyl-N'-2-aminoethyl-1,2-ethanediamine (tert-Me-TETA). sec-Me-TETA and tert-Me-TETA are depicted in scheme 2 as compounds 2 and 3 respectively.

Hydrogenating (hydrogenation) in the context of the present invention means the reaction of the aminonitrile BCMI with hydrogen. Processes for preparing biscyanomethylimidazolidine (BCMI) are known in principle to those skilled in the art. BCMI is preferably prepared by reacting ethylenediaminediacetonitrile (EDDN) and formaldehyde. This reaction is preferably effected in batchwise mode. BCMI can optionally also be prepared in continuous mode, for example with an excess of formaldehyde. It is possible here to use water as a solvent; a typical temperature is 60° C. and a typical residence time 6 minutes.

The water present in the BCMI-containing reaction mixture can preferably be removed by a distillation. To perform such a distillation, as well as columns with random packing or tray columns, it is also possible to use thin-layer evaporators (thin-film evaporators). Preference is given to distilling water in a thin-layer evaporator. Suitable thin-layer evaporators are known to those skilled in the art (see also Ullmanns Enzyklopädie der technischen Chemie, volume 2, fourth edition, Verlag Chemie, Weinheim (1972), page 656-657). Preferred thin-layer evaporators are of the "Sambay", "Luwa" or "Sako" type, particular preference being given to a Sambay thin-layer evaporator. Optionally, to remove water from the BCMI-containing reaction mixture, apart from distillation, it is also possible to perform further water removal steps such as extraction, drying, filtration, etc.

The catalysts used for hydrogenation of the two nitrile functions of the BCMI to the amine may be catalysts which comprise, as the active species, one or more elements of transition group 8 of the periodic table (Fe, Co, Ni, Ru, Rh, Pd, Os, Ir, Pt), preferably Fe, Co, Ni, Ru or Rh, more preferably Co or Ni. This includes so-called skeletal catalysts (also referred to as Raney® type; hereinafter also: Raney catalyst), which are obtained by leaching (activating) an alloy of hydrogenation-active metal and a further component (preferably Al). The catalysts may additionally comprise one or more promoters. In a preferred embodiment, Raney catalysts are used in the process according to the invention, preferably Raney cobalt or Raney nickel catalysts, and more preferably Raney cobalt catalysts doped with at least one of the elements Cr, Ni or Fe, or Raney nickel catalysts doped with one of the elements Mo, Cr or Fe.

The catalysts can be used as unsupported catalysts or in supported form. The supports employed are preferably metal oxides such as $Al_2O_3$, $SiO_2$, $ZrO_2$, $TiO_2$, mixtures of metal oxides or carbon (activated carbons, carbon blacks, graphite).

Before use, the oxidic catalysts are activated outside the reactor or in the reactor by reduction of the metal oxides in a hydrogen-comprising gas stream at elevated temperature. When the catalysts are reduced outside the reactor, this can be followed by a passivation by an oxygen-comprising gas stream or embedding into an inert material, in order to prevent uncontrolled oxidation under air and to enable safe handling. The inert materials used may be organic solvents such as alcohols, but also water or an amine, preferably the reaction product. An exception in the activation step is that of the skeletal catalysts, which can be activated by leaching with aqueous base, as described, for example, in EP-A 1 209 146.

According to the process performed (suspension hydrogenation, fluidized bed process, fixed bed hydrogenation), the catalysts are used in the form of powder, spall or shaped bodies (preferably extrudates or tablets).

Particularly preferred fixed bed catalysts are the unsupported cobalt catalysts disclosed in EP-A1 742 045, doped with Mn, P and alkali metal (Li, Na, K, Rb, Cs). The catalytically active material of these catalysts consists, before the reduction with hydrogen, of 55 to 98% by weight, especially 75 to 95% by weight, of cobalt, 0.2 to 15% by weight of phosphorus, 0.2 to 15% by weight of manganese and 0.05 to 5% by weight of alkali metal, especially sodium, calculated in each case as the oxide.

Further suitable catalysts are the catalysts which are disclosed in EP-A 963 975, and whose catalytically active material, before the treatment with hydrogen, comprises 22 to 40% by weight of $ZrO_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or manganese, calculated as $Al_2O_3$ and $MnO_2$ respectively, and no oxygen compounds of molybdenum, for example, the catalyst A disclosed in this document with the composition of 33% by weight of Zr, calculated as $ZrO_2$, 28% by weight of Ni, calculated as NiO, 11% by weight of Cu, calculated as CuO, and 28% by weight of Co, calculated as CoO.

Also suitable are the catalysts which are disclosed in EP-A 696 572 and whose catalytically active material, before the reduction with hydrogen, comprises 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or manganese, calculated as $Al_2O_3$ and $MnO_2$ respectively, for example the catalyst disclosed specifically in this document with the composition of 31.5% by weight of $ZrO_2$, 50% by weight of NiO, 17% by weight of CuO and 1.5% by weight of $MoO_3$. Likewise suitable are the catalysts which are described in WO-A 99/44984 and comprise (a) iron or a compound based on iron or mixtures thereof, (b) from 0.001 to 0.3% by weight, based on (a), of a promoter based on 2, 3, 4 or 5 elements selected from the group of Al, Si, Zr, Ti, V, (c) from 0 to 0.3% by weight, based on (a), of a compound based on an alkali metal and/or alkaline earth metal, and (d) from 0.001 to 1% by weight, based on (a), of manganese.

For suspension processes, preference is given to using Raney catalysts. In the case of the Raney catalysts, the active catalyst is prepared as 'metal sponge' from a binary alloy (nickel, iron, cobalt, with aluminum or silicon) by leaching out one partner with acid or alkali. Residues of the original alloy partner often have a synergetic effect.

The Raney catalysts used in the process according to the invention are preferably prepared proceeding from an alloy of cobalt or nickel, more preferably cobalt, and of a further alloy component which is soluble in alkalis. For this soluble alloy component, preference is given to using aluminum, but it is also possible to use other components such as zinc and silicon or mixtures of such components.

To activate the Raney catalyst, the soluble alloy component is extracted completely or partly with alkali, for which purpose, for example, aqueous sodium hydroxide can be used. The catalyst can then be washed, for example, with water or organic solvents.

Individual or plural further elements may be present in the catalyst as promoters. Examples of promoters are metals of transition groups IB, VIB and/or VIII of the Periodic Table, such as chromium, iron, molybdenum, nickel, copper, etc.

Activation of the catalysts by leaching out the soluble component (typically aluminum) can be effected either in the reactor itself or before introduction into the reactor. The pre-activated catalysts are air-sensitive and pyrophoric and are therefore generally stored and handled under a medium, for example water, an organic solvent or a substance which is present in the inventive reaction (solvent, reactant, product), or embedded into an organic compound which is solid at room temperature.

In a preferred embodiment, in accordance with the invention, a Raney cobalt skeletal catalyst is used, which has been obtained from a Co/Al alloy by leaching with aqueous alkali metal hydroxide solution, for example sodium hydroxide solution, and subsequently washing with water, and preferably comprises, as promoters, at least one of the elements Fe, Ni or Cr.

Such catalysts typically comprise, as well as cobalt, also 1 to 30% by weight of Al, particularly 2 to 12% by weight of Al, very particularly 3 to 6% by weight of Al, 0 to 10% by weight of Cr, particularly 0.1 to 7% by weight of Cr, very particularly 0.5 to 5% by weight of Cr, especially 1.5 to 3.5% by weight of Cr, 0 to 10% by weight of Fe, particularly 0.1 to 3% by weight of Fe, very particularly 0.2 to 1% by weight of Fe, and/or 0 to 10% by weight of Ni, particularly 0.1 to 7% by weight of Ni, very particularly 0.5 to 5% by weight of Ni, especially 1 to 4% by weight of Ni, where the weight data are based in each case on the total catalyst weight.

The catalyst used in the process according to the invention may, for example, advantageously be a "Raney 2724" cobalt skeletal catalyst from W. R. Grace & Co. This catalyst has the following composition:

Al: 2 to 6% by weight, Co: ≥86% by weight, Fe: 0 to 1% by weight, Ni: 1 to 4% by weight, Cr: 1.5 to 3.5% by weight.

It is likewise possible in accordance with the invention to use a nickel skeletal catalyst which has been obtained from an Ni/Al alloy by leaching with aqueous alkali metal hydroxide solution, for example sodium hydroxide solution, and subsequent washing with water, and preferably comprises, as promoters, at least one of the elements Fe, Cr.

Such catalysts typically comprise, as well as nickel, also
1 to 30% by weight of Al, particularly 2 to 20% by weight of Al, very particularly 5 to 14% by weight of Al,
0 to 10% by weight of Cr, particularly 0.1 to 7% by weight of Cr, very particularly 1 to 4% by weight of Cr, and/or
0 to 10% by weight of Fe, particularly 0.1 to 7% by weight of Fe, very particularly 1 to 4% by weight of Fe,
where the weight data are based in each case on the total catalyst weight.

The catalyst used in the process according to the invention may, for example, advantageously be an A 4000 nickel skeletal catalyst from Johnson Matthey. This catalyst has the following composition:

Al: ≤14% by weight, Ni: ≥80% by weight, Fe: 1 to 4% by weight, Cr: 1 to 4% by weight.

In the event of declining activity and/or selectivity, the catalysts can optionally be regenerated by the methods known to those skilled in the art, as published, for example, in WO 99/33561 and the documents cited therein.

The regeneration of the catalyst can be performed in the actual reactor (in situ) or on the deinstalled catalyst (ex situ). In the case of fixed bed processes, preference is given to regenerating in situ; in suspension processes, preference is given to removing a portion of the catalyst continuously or discontinuously, regenerating it ex situ and returning it.

The temperatures at which the hydrogenation is performed are within a range from 40 to 150° C., preferably from 70 to 140° C., especially 80 to 140° C.

The pressure in the course of hydrogenation is generally 5 to 300 bar, preferably 30 to 250 bar, more preferably 40 to 160 bar.

In a preferred embodiment, BCMI is supplied to the hydrogenation at a rate which is not greater than the rate at which BCMI reacts with hydrogen in the hydrogenation. The feed rate should preferably be adjusted such that virtually full conversion is achieved. This is influenced by temperature, pressure, type of mixture, type and amount of catalyst and of reaction medium, mixing quality of the reactor contents, residence time, etc.

The hydrogenation is preferably performed in the presence of a solvent, for example an organic solvent. Optionally, the hydrogenation can also be performed in the presence of water, since complete removal of water before the hydrogenation is unnecessary. For example, the hydrogenation can be performed in an organic solvent which comprises water in traces or as a secondary component. The use of water as a solvent alone or of solvent mixtures with a water excess is possible, but is less suitable than the use of an organic solvent alone or in excess.

A suitable solvent, which may comprise one or more components, should preferably have the following properties:
(a) the solvent should have a stabilizing effect on BCMI, especially prevent the decomposition thereof at the prevailing temperatures;
(b) the solvent should exhibit good hydrogen solubility;
(c) the solvent should be inert under the reaction conditions;
(d) the reaction mixture (BCMI, any water and solvent) should be monophasic under reaction conditions;
(e) the solvent should be selected with regard to a preferably distillative removal of the product from the product stream after the hydrogenation. Energy- or apparatus-intensive (for example close-boiling mixtures or azeotropes which are difficult to separate) separations should be avoided.
(f) the solvent should have good removability from the products, i.e. the boiling temperature should differ sufficiently from that of the products. In this context, a lower boiling temperature than that of the products is preferred.

Preferred solvents are organic solvents, for example amides such as N-methylpyrrolidone (NMP) and dimethylformamide (DMF), aromatic and aliphatic hydrocarbons such as benzene, toluene and xylene, alcohols such as methanol, ethanol, propanol, isopropanol, butanol, isobutanol, secondary butanol and tertiary butanol, amines, esters such as methyl acetate or ethyl acetate, and ethers such as diisopropyl ether, diisobutyl ether, glycol dimethyl ether, diglycol dimethyl ether, dioxane and tetrahydrofuran (THF). Preference is given to using ethers in the process according to the invention, more preferably cyclic ethers and especially preferably tetrahydrofuran or 2-methyltetrahydrofuran (2-Me-THF). In a further preferred embodiment, alcohols, especially methanol, are used as the organic solvent.

The use of an organic solvent (inert organic compound) is found to be advantageous, since this can achieve stabilization of the individual components of the (optionally aqueous) aminonitrile mixture, especially in the presence of the resulting amines. Moreover, the use of organic solvents allows a rinsing effect (reduction in the rinse cycles, reduction of catalyst discharge) on the catalyst used to be achieved, which can increase the service life thereof or reduce the consumption thereof (longer catalyst lifetime), and improve the catalyst space velocity. The use of suitable solvents can also reduce the formation of further by-products such as AEPip.

The solvent is used in a weight ratio relative to the aminonitrile used (BCMI) of 0.1:1 to 15:1. The concentration of the aminonitrile mixture in the solution in which the hydrogenation is performed should be selected such that a suitable feed rate or residence time can be established. It is preferred to mix 5 to 50% by weight of the aminonitrile with the solvent. Based on the particularly preferred methanol or THF or 2-Me-THF solvents, it is advantageous, for example, to use 20 to 40% by weight of the aminonitrile based on the solvent.

The proportion of water in the solution is normally within a range from 0 to 50% by weight, preferably 0 to 30% by weight, especially ≤5% by weight. The hydrogenation is more preferably performed under anhydrous conditions (water content ≤0.1% by weight). The stated amounts of water are based on the aminonitrile.

Optionally, additional additives may be present in the solution in which the hydrogenation is performed. Useful additives include in principle hydroxides such as alkali metal hydroxides, alkoxides, amides, amines. Additives suitable with preference are amines, particularly EDA and ammonia, especially EDA. Moreover, it is also possible for acidic additives, for example silicates, to be additionally present in the solution. These substances can be added as a pure substance or dissolved in a solvent. The process according to the invention is preferably performed with addition of additives.

In one embodiment of the process, no ammonia is added to the solution in which the hydrogenation is performed. When ammonia is still dissolved in the reactants or in the aqueous solution which may be used, or is released as a by-product in the hydrogenation, this is not troublesome. Any ammonia present can be removed by methods known to those skilled in the art, for example by distillation. When ammonia is dispensed with, this has the advantage that the autogenous pressure of the system is reduced.

In the process according to the invention, it is possible to use one solvent (or more than one), in which case the solvent is first mixed with BCMI. The resulting solution, which may optionally also comprise additives, is subsequently fed into the reaction vessel comprising the catalyst. Optionally, for example in semibatchwise processes, a portion of the solvent can be initially charged in the reaction vessel together with the catalyst, and then the solution is metered in. In continuous processes, a portion of the solvent can also be added to the reaction vessel separately from the solution which comprises BCMI, the solvent and if appropriate the additive. In a preferred embodiment, the BCMI present in the solution is fed in at a rate which is not greater than the rate with which BCMI reacts with hydrogen in the hydrogenation. Optionally, for example in the case of semibatchwise processes, a portion of the solvent can be initially charged in the reaction vessel together with the catalyst, and then the solution is metered in.

In a preferred embodiment of the present invention, the hydrogenation of BCMI in a semibatchwise process is effected with a Raney cobalt catalyst. The solvent used is preferably 2-Me-THF, the temperature is 120° C. and the pressure is 100 bar. The catalyst is initially charged in 2-Me-THF and the aminonitrile (BCMI) is metered in as an 18% solution within 2 h.

The process according to the invention for preparing Me-TETA by hydrogenating BCMI can be performed in customary reaction vessels suitable for catalysis in a fixed bed mode, fluidized bed mode or suspension mode, and continuously, semicontinuously or batchwise. Suitable reaction vessels for performance of the hydrogenation are those in which contacting of the aminonitrile and of the catalyst with the gaseous hydrogen is possible under pressure.

The hydrogenation in suspension mode can be performed in a stirred reactor, jet loop reactor, jet nozzle reactor, bubble column reactor, or in a cascade of identical or different reactors of these types. For the hydrogenation over a fixed bed catalyst, tubular reactors but also tube bundle reactors are conceivable.

In the case of a fixed bed catalyst, it is contacted with the aminonitrile in liquid phase or trickle mode. Preference is given, however, to using the suspension mode in semicontinuous mode and preferably in continuous mode.

The hydrogenation of the nitrile groups takes place with release of heat, which generally has to be removed. The heat can be removed by means of installed heat transferor surfaces, cooling jackets or external heat transferors in a circulation system around the reactor. The hydrogenation reactor or a hydrogenation reactor battery can be operated in straight pass. Alternatively, a circulation mode is also possible, in which a portion of the reactor discharge is recycled to the reactor inlet, preferably without preceding workup of the circulation stream. This allows optimal dilution of the reaction solution to be achieved. More particularly, the circulation stream can be cooled in a simple and inexpensive manner by means of an external heat transferor, and the heat of reaction can thus be removed. The reactor can thus also be operated adiabatically, in which case the temperature rise of the reaction solution can be restricted by the cooled circulation stream. Since the reactor itself then need not be cooled, a simple and inexpensive design is possible. One alternative is that of a cooled tube bundle reactor (only in the case of the fixed bed). A combination of the two modes is also conceivable. In this case, a fixed bed reactor is preferably connected downstream of a suspension reactor.

As already stated above, in the process according to the invention, at least one Me-TETA is prepared as the main product in the hydrogenation. In addition, in the process according to the invention, the hydrogenation reaction mixture may also comprise by-products, such as shorter ethyleneamines (for example diethylenetriamine/DETA), high boilers, a cyclic compound (such as AEPip—aminoethylenepiperazine) or (unsubstituted) TETA as such. Processes for removing these by-products and processes for separating an Me-TETA mixture which comprises one or more of the Me-TETAs as shown in scheme 2 are known to those skilled in the art. The removal of by-products from and/or the separation of an Me-TETA mixture can be effected, for example, by distillation or as a chromatographic separation process. This can optionally be done in combination and/or in more than one stage.

The EDDN used to prepare BCMI can in principle be prepared by methods known to those skilled in the art; see, for example, WO 2008/104582. Normally, EDDN is prepared by reaction of EDA with formaldehyde and hydrogen cyanide (HCN). The molar ratio of EDA to formaldehyde to HCN is preferably 1:1.5:1.5 to 1:2:2 [mol/mol/mol].

Unless stated otherwise below (option i) to iv)), the reactant components for EDDN preparation can be added to the particular reaction vessel in any desired sequence.

For example, one reactant can be initially charged completely and a second reactant can be added. EDDN can preferably be prepared according to one of the options i) to iv) detailed below. Particular preference is given to preparing EDDN by option i).

In option i), formaldehyde and HCN are first converted to formaldehyde cyanohydrin (FACH), and then EDA is reacted in turn with FACH and the molar ratio of EDA to FACH is 1:1.5 to 1:2 [mol/mol]. EDA, formaldehyde and HCN are commercially available products or can in principle be prepared by methods known to those skilled in the art. EDA is preferably used in the process according to the invention in the form of its free base, but it is optionally also possible to use salts such as the dihydrochloride of EDA as the reactant.

The conversion of formaldehyde and HCN is known to the person skilled in the art. FACH can be prepared by reacting aqueous formaldehyde with hydrogen cyanide. Formaldehyde is preferably present as a 30 to 50% aqueous solution; hydrogen cyanide is preferably used in 90 to 100% purity. This reaction is effected preferably at a pH of 5.5, which is preferably established with sodium hydroxide solution or ammonia. The reaction can be effected at temperatures of 20 to 70° C., for example in a loop reactor and/or tubular reactor.

Instead of purified hydrogen cyanide (HCN), it is also possible for crude HCN gas in aqueous formaldehyde solution to be chemisorbed under the above-mentioned conditions to give FACH. The crude HCN gas is preferably prepared by pyrolysis of formamide and comprises, as well as water, small proportion of ammonia in particular.

Optionally, the aqueous FACH solution obtained can be concentrated by gentle vacuum concentration, for example with a falling-film or thin-layer evaporator, and freed of low boilers, especially of hydrogen cyanide. Preference is given to a concentration to a 50-80% FACH solution. Before the concentration, stabilization of the FACH solution by lowering the pH to ≤4, preferably to ≤3, is advantageous, for example by addition of acid, for example by addition of phosphoric acid or preferably of sulfuric acid.

The molar ratio of EDA to FACH in option i) is preferably about 1:1.8 to 1:2 [mol/mol], especially approx. 1:2 [mol/mol].

In option ii), EDDN is converted by reacting an ethylenediamine-formaldehyde adduct (EDFA) with hydrogen cyanide (HCN), where the molar ratio of EDFA to HCN is 1:1.5 to 1:2 [mol/mol]. The molar ratio of EDFA to HCN is preferably 1:1.8 to 1:2 [mol/mol], especially approx. 1:2 [mol/mol]. EDFA is preferably prepared by mixing approximately equimolar amounts of EDA and formaldehyde.

In option iii), EDA is reacted with a mixture of formaldehyde and hydrogen cyanide (MFH), where the molar ratio of EDA to MFH is 1:1.5 to 1:2 [mol/mol]. The molar ratio of EDA to MFH is 1:1.8 to 1:2 [mol/mol], especially approx. 1:2 [mol/mol]. The MFH is preferably prepared by mixing approximately equimolar amounts of formaldehyde and hydrogen cyanide.

In option iv), EDA is reacted with formaldehyde and hydrogen cyanide (HCN) in a timely manner (in parallel), where the molar ratio of EDA to formaldehyde to HCN is 1:1.5:1.5 to 1:2:2 [mol/mol/mol]. The molar ratio of EDA to formaldehyde to HCN is 1:1.8:1.8 to 1:2:2 [mol/mol/mol], especially approx. 1:2:2 [mol/mol/mol]. Preferably, in this embodiment, the three reactant components are added to the reaction vessel simultaneously or stepwise in equal molar portions based on the particular total amount of reactant.

Under some circumstances, the particular reactants or intermediates can be used in the process according to the invention directly after the preparation thereof. For example, in option i), FACH can be used as a reactant in the process according to the invention without preceding isolation. Optionally, however, FACH can first be isolated after the preparation thereof, in order then to be used in the process according to the invention.

In one embodiment of the present invention, the EDDN preparation is performed without or at least essentially without cyano salts such as KCN.

The EDDN preparation is normally performed in the presence of a solvent. In the process according to the invention for preparing EDDN, preference is given to converting the reactants in aqueous phase. Optionally, as well as water, it is also possible to use further solvents which are known to those skilled in the art and are water-miscible. Less preferred, however, is the use of alcohols, especially methanol, as solvents.

The EDDN preparation is preferably performed at a temperature of 10 to 90° C., especially at 30 to 70° C. The reaction can be performed at standard pressure or optionally also under elevated pressure. The EDDN preparation is preferably performed in a tubular reactor or a stirred tank battery. The EDDN preparation can preferably also be performed as a continuous process, especially as an industrial scale process.

When the corresponding mononitrile ethylenediaminemonoacetonitrile (EDMN) is formed as a by-product in the preparation of EDDN, it can preferably be removed after the EDDN synthesis by methods known to those skilled in the art. Optionally, however, it is also possible to use an aminonitrile mixture comprising EDDN and EDMN in the process according to the invention. The conversion products formed from EDMN in the subsequent reaction with formaldehyde or the hydrogenation can likewise be removed from BCMI and Me-TETA by methods known to those skilled in the art. Preference is given, however, to effecting the EDDN preparation in such a way that a small proportion of EDMN is present. The content of EDMN and of any further by-products, for example other aminonitriles, is preferably ≤10% by weight, especially ≤5% by weight, based on EDDN.

After the EDDN preparation or optionally after the BCMI preparation, in the process according to the invention, a low boiler removal can be performed before the hydrogenation. When FACH is used to prepare EDDN, the low boiler removal can be effected actually before the reaction of FACH with EDA. Preference is given to removing hydrogen cyanide (HCN) as a low boiler. HCN can also occur as a decomposition product of FACH. In addition, any ammonia can be removed at this point. Preference is given to effecting the removal by distillation, for example in the form of a thin-film evaporation, for example a Sambay distillation. Optionally, the reaction mixture can also be stripped with nitrogen.

Apart from the low boiler removal, a purification step by adsorption of impurities on an absorbent, for example activated carbon or ion exchanger, can be carried out with the EDDN and/or the BCMI. This can be effected, for example, in an absorption column filled with the absorbent.

The present invention further provides for the use of the inventive Me-TETAs, especially the use of mono-Me-TETAs. The inventive Me-TETAs can be used for producing coatings, adhesion promoters, adhesives, composites, plastic, cellulose-based chemicals, paper auxiliaries or auxiliaries for obtaining or extracting oil, coal or gas.

The examples which follow illustrate the present invention.
Aminonitrile Synthesis

EXAMPLE 1

BCMI Synthesis

A solution of EDDN (50.0 g, 360 mmol) in formaldehyde (36.0 g, 360 mmol, 30% by weight in $H_2O$) is stirred in a three-neck flask at 90° C. for 15 min and then cooled in an ice bath. By means of a Sambay apparatus, the water is removed at 75° C. and 50 mbar down to a residual content of 1.5% by weight. For further removal of water, the distillate is taken up in $CH_2Cl_2$ (60 ml), and the solution is dried over $Na_2SO_4$, filtered and concentrated on a rotary evaporator. The BCMI target compound (46.0 g, 307 mmol, residual water content 0.1% by weight) is obtained in analytic pure form as an orange oil.

Hydrogenation
General:

The hydrogenation is effected in 2-Me-THF as a solvent at 120° C. and 100 bar in a semibatchwise process. To this end, the Raney-Cobalt 2724 catalyst from Grace Division is initially charged in 2-Me-THF, and a solution of the particular aminonitriles in 2-Me-THF is metered in over 120 min and the mixture is stirred for a further 60 min. For the evaluation of the tests, an internal standard (DEGDME) is also metered in. For analysis, the biphasic reaction discharge is homogenized with methanol. The evaluation is effected in % by weight.

Analysis Method for Identification of the Components of the Particular Reaction Mixtures:
Column: DB 1, 60 m, 0.32 mm, 1.0 μm Gas chromatograph: HP 5890 with autosampler
Injector temperature: 250° C.
Detector temperature: 300° C.
Temperature program: 200° C.-15 min isothermal-5° C./min-280° C.
Internal standard: DEGDME
Evaluation: HP ChemStation

EXAMPLE 2

BCMI Hydrogenation

A 300 ml Miniplant autoclave with devices for ensuring pressure and temperature is initially charged with 4.7 g of Ra—Co 2724 from Grace Division in 40 g of 2-Me-THF. The autoclave is heated to 120° C. and hydrogen is injected up to a total pressure of 100 bar. Within 120 min, a mixture of 18 g of BCMI, 1.8 g of DEGDME and 98 g of 2-Me-THF is metered in. The reaction mixture is stirred under reaction conditions for a further 60 min. The discharge is homogenized by means of methanol and analyzed by means of GC. The following selectivities are found: 44.5% tert-Me-TETA, 47.2% sec-Me-TETA, 6.4% TETA and 1.3% AEPIP.

The invention claimed is:

1. A process for preparing triethylenetetramine substituted by at least one methyl group (Me-TETA), comprising the hydrogenation of biscyanomethylimidazolidine (BCMI) in the presence of a catalyst.

2. The process according to claim 1, wherein the Me-TETA is triethylenetetramine substituted by one methyl group (mono-Me-TETA), triethylenetetramine substituted by two methyl groups (bis-Me-TETA), or triethylenetetramine substituted by three methyl groups (tris-Me-TETA).

3. The process according to claim 1, wherein the Me-TETA is N-2-aminoethyl-N'-(2-N''-methylaminoethyl)-1,2-ethanediamine (sec-Me-TETA) or N-2-aminoethyl-N-methyl-N'-2-aminoethyl-1,2-ethanediamine (tert-Me-TETA).

4. The process according to claim 1, wherein the hydrogenation of BCMI gives a mixture comprising at least 2 Me-TETAs.

5. The process according to claim 4, wherein at least one Me-TETA is isolated from the Me-TETA mixture obtained in the hydrogenation.

6. The process according to claim 1, wherein the catalyst used is a Raney catalyst.

7. The process according to claim 6, wherein the Raney catalyst is a Raney nickel or Raney cobalt catalyst.

8. The process according to claim 6, wherein the Raney catalyst is a Raney cobalt skeletal catalyst which has been obtained from a Co/Al alloy by leaching with aqueous alkali metal hydroxide solution and which comprises, as a promoter, at least one of the elements Fe, Ni or Cr.

9. The process according to claim 1, wherein the hydrogenation is performed in the presence of a solvent.

10. The process according to claim 9, wherein the solvent is 2-methyltetrahydrofuran (2-Me-THF), tetrahydrofuran (THF) or methanol.

11. The process according to claim 1, wherein the pressure is 30 to 250 bar or the temperature is 80° C. to 140° C.

12. The process according to claim 1, wherein the hydrogenation is performed in the presence of an additive.

13. The process according to claim 12, wherein the hydrogenation is performed in the presence of an additive in the presence of ethylenediamine (EDA) or ammonia.

14. The process according to claim 1, wherein BCMI is prepared by reaction of ethylenediaminediacetonitrile (EDDN) and formaldehyde.

15. The process according to claim 14, wherein water present in the BCMI-containing reaction mixture is removed by a distillation.

16. The process according to claim 15, wherein a thin-film evaporator is used for distillation of water.

17. The process according to claim 14, wherein EDDN is prepared by reacting ethylenediamine (EDA) with formaldehyde and hydrogen cyanide (HCN).

18. The process according to claim 17, wherein the EDDN preparation is performed according to one of the options i) to iv), in which
   i) formaldehyde and HCN are first converted to formaldehyde cyanohydrin (FACH) and then EDA is reacted with FACH, where the molar ratio of EDA to FACH is 1:1.5 to 1:2 [mol/mol], or
   ii) an ethylenediamine-formaldehyde adduct (EDFA) is reacted with HCN, where the molar ratio of EDFA to HCN is 1:1.5 to 1:2 [mol/mol], or
   iii) EDA is reacted with a mixture of formaldehyde and hydrogen cyanide (MFH), where the molar ratio of EDA to MFH is 1:1.5 to 1:2 [mol/mol], or
   iv) EDA is reacted simultaneously with formaldehyde and HCN, where the molar ratio of EDA to formaldehyde to HCN is 1:1.5:1.5 to 1:2:2 [mol/mol/mol].

* * * * *

UNITED STATES PATENT AND TRADEMARK OFFICE
CERTIFICATE OF CORRECTION

PATENT NO. : 8,586,795 B2  Page 1 of 1
APPLICATION NO. : 13/378091
DATED : November 19, 2013
INVENTOR(S) : Hugo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 49 days.

Signed and Sealed this
Twenty-second Day of September, 2015

Michelle K. Lee
*Director of the United States Patent and Trademark Office*